(12) United States Patent
Strebhardt et al.

(10) Patent No.: US 6,180,380 B1
(45) Date of Patent: Jan. 30, 2001

(54) CLONING OF A NEW MEMBER OF THE SERINE THREONINE KINASE FAMILY

(75) Inventors: Klaus Strebhardt, Frankfurt; Helga Rübsamen-Waigmann, Bad Soden; Uwe Holtrich, Kelkheim, all of (DE)

(73) Assignee: Bayer Aktiengesellschaft, Luverkusen (DE)

( * ) Notice: Under 35 U.S.C. 154(b), the term of this patent shall be extended for 0 days.

(21) Appl. No.: 09/198,122

(22) Filed: Nov. 23, 1998

Related U.S. Application Data

(62) Division of application No. 08/601,014, filed as application No. PCT/EP94/02863 on Aug. 30, 1994, now abandoned.

(30) Foreign Application Priority Data

Aug. 30, 1993 (DE) ................................................ 43 29 177

(51) Int. Cl.[7] .................................................... C12N 9/12
(52) U.S. Cl. .......................... 435/194; 435/183; 435/69.1; 530/350
(58) Field of Search .................................... 435/194, 183, 435/69.1; 530/350

(56) References Cited

PUBLICATIONS

Golsteyn et al. (1994) J. Cell Science, 107:1509–1517.*
Database GenBank/Swiss–Prot on STN, (1994) Golsteyn et al. Accession No. P53350.*
Proceedings of the National Academy of Sciences of USA, vol. 90, Nr. 11 (1993) pp. 4882–4886. (Clay et al.).
EMBL Databank HSPLK1 (1993), Golsteyn et al "Cloning and characterization of anovel human protein kinas plk–1 a potential homolog of Drosophila polo Saccharomyces cerevisiae CDC5 two genes implicated in regulating progression through mitosis" ACx73458.
Genes & Development, vol. 5, Nr. 12a (1990) pp. 2153–2165 (Llamazares et al.).
Cell Growth & Differentiation, vol. 5, Nr. 3 (1994) pp. 249–257 (Hamanaka et al.).
Proceedings of the National Academy of Sciences of USA, vol. 91, Nr. 5 (1994) pp. 1736–1740 (Holtrich et al.).
EMBL Databank HSPLKSTK (1994) Holrich et al, Induction and down–regulation of PLK, a human serine/threonine kinase expressed in proliferating cellsa dn tumors AC X75932.
"Molecular Cloning, A Laboratory Manual, 2d Edition", J. Sambrook et al (1989) Cover and the title pages only.
Crews et al, "Mouse Erk–1 gene product is a serine/threonine protein kinase that has the potential to phosphorylate tyrosine" Proc.Natl.Acad.Sci. USA, vol. 88 (1991) pp. 8845–8849.
Ben–David et al, "A mammalian protein kinase with potential for serine/threonine and tyrosine phosphorylation is related to cell cycle regulators", The EMBO Journal, vol. 10, No. 2, pp. 317–325 (1991).
Parker et al, "Cyclin promotes the tyrosine phosphorylation of $p34^{cdc2}$ in a wee1* dependent manner", The EMBO Journal, vol. 10, No. 5, pp. 1255–1263 (1991).
Parker et al, "Inactivation of the $p34^{cdc2}$–Cyclin B Comples by the Human WEE1 Tyrosine Kinase", Science, vol. 257 (1992), pp. 1955–1957.
Coleman et al, "Negative Regulation of the Wee1 Protein Kinase by Direct Action of the Nim1/Cdr1 Mitotic Inducer", Cell, vol. 72 (1993) pp. 919–929.
Chirgwin et al, "Isolation of Biologically Active Ribonucleic Acid from Sources Enriched in Ribonuclease", Biochemistry, vol. 18, No. 24 (1979) 5294–5299.
Haim Aviv et al, "Purification of Biologically Active Globin Messenger RNA by Chromatography on Oligothymidylic acid–Cellulose", Proc.Nat.Acad.Sci. USA, vol. 69, No. 6, pp. 1408–1412 (1972).
Gubler et al, A simple and very efficient method for genrating cDNA libraries), Gene. 25 (1983) 263–269.
Lake et al. (Dec. 1993) Molec.Cell.Biol., vol. 13, No. 12,pp.7793–7801.

* cited by examiner

Primary Examiner—Enrique D. Longton
(74) Attorney, Agent, or Firm—Norris, McLaughlin & Marcus, P.A.

(57) ABSTRACT

The invention relates to a PLK protein, which is characterized in that it comprises (a) the amino acid sequence shown in SEQ ID No: 1 or
   (b) variants of the sequence from (a).

1 Claim, 1 Drawing Sheet

CLONING OF A NEW MEMBER OF THE SERINE THREONINE KINASE FAMILY

This application is a divisional of application Ser. No. 08/601,014, filed on Feb. 23, 1996 abandoned; which is a 371 of PCT/EP94/02863 filed on Aug. 30, 1994.

The present invention relates to a new serine threonine kinase, the gene coding therefor and the detection of changes in this gene and its products in human tumours.

The activation of intracellular biochemical networks as a response to external stimuli leads to coordinated control of growth and of differentiation in eukaryotes. Protein kinases are known as constituents of many signal transduction pathways. In this connection, these kinases phosphorylate their normal physiological substrates and are regulated in their enzymatic activity by interaction with other kinases and phosphatases. The identification of a large number of protein kinases in many eukaryotic cells of mammals, yeast and Drosophila makes it probable that findamental cellular differentiation and growth processes are controlled by identical mechanisms in a wide spectrum of organisms.

In eukaryotes, all protein kinases known until now phosphorylate the hydroxyamino acids serine, threonine or tyrosine. Phosphorylation by these kinases plays a prominent role in the control of mitosis and cellular differentiation. Receptors for numerous polypeptide growth factors are transmernbrane tyrosine kinases which, for their parts, phosphorylate serine/threonine kinases such as protein kinase C, MP kinase and p74raf The central component of the cell cycle machinery is the serine/threonine kinase p34cdc2, which has originally been isolated as a product of the mitosis gene cdc2 (cell division cycle) from *Schizosaccharomyces pombe* and CDC28 from *Saccharomyces cerevisiae*. The activity of p34cdc2 is regulated by interaction with cyclins. In the G1 phase, the start of the cell cycle, p34cdc2 is not associated with cyclins and has no kinase activity. If cells are supplied with sufficient nutrients, G1 cyclin accumulates which, by association, initiates the kinase activity of p34cdc2. By this means "start" is exceeded and the change in the cell cycle (DNA replication, formation of the MTOC, microtubule organizing centre) is initiated. In this connection, the synthesis of cyclin B also begins, which then binds to p34cdc2. This complex is inactive, since the binding of cyclin B induces the phosphorylation of p34cdc2 on tyrosine 15, whereby the kinase activity is inhibited. The inactive complex, which is also called preMPF (maturation promoting factor), is also phosphorylated on threonine 160. This phosphorylation is necessary for the MPF activity, but not sufficient in order to abolish the inhibitory (effects of tyrosine phosphorylation. The subsequent dephosphorylation of p34cdc2 during the late G2 phase of the cell cycle activates MPF and leads to the induction of mitosis (M phase). The post-translational reactions, which underlie a complex physiological control, play an essential part in the temporal regulation of the MPF activity. The protein tyrosine kinase weel was originally isolated from *Schizosaccharomyces pombe* and inhibits, via the mechanism described, entry into mitosis, while the product of the cdc25 gene promotes the start of mitosis. Active MPF activates tyrosine phosphatase and inhibits protein tyrosine kinase, which modify p34cdc2, whereby MPF is completely activated explosively, such that cells are driven into mitosis very rapidly and irreversibly.

The most recent investigations of the cell cycle show that essential regulators of the cell cycle are involved in carcinogenesis. This is not surprising because constant proliferation of cells is an outstanding feature of tumours. Changes to cyclin A, which binds both to p34cdc2 and to p34cdc2-related protein kinase, can cause the transfornation of cells. The cyclin A gene is the integration site for a fragment of the hepatitis B virus genome in a human hepatocarcinoma. Moreover, cyclin A is associated with the transforming protein E1A in adenovirus-transformed cells. Cyclin A is possibly a target protein of E1A, since it is associated in the S phase with the transcription factor E2F in a complex which has lower transcription activity than free E2F. A further constituent of this complex is p34cdc2. The connection with gene expression is produced in this way. E1A can destroy this complex, whereby E2F is released. Thus certain genes can be regulated which are important for the transformed phenotype.

Moreover, there are further relationships between oncoproteins, tumour suppressor gene products and cyclin-p34cdc2 complexes. The mos oncoprotein is likewise a serine/threonine kinase. The c-mos protein from Xenopus is a component of the cytostatic factor, which is necessary for the stabilization of the activated cyclin B-p34cdc2 in growth-inhibited Xenopus eggs. The role of the mos protein, however, is still unclear, as it does not appear to phosphorylate the complex in vivo. On the one hand, c-mos stabilizes the activated cyclin B-P34cdc2 complex, whereby the mitosis activity of the cells is inhibited, and on the other hand it promotes the cell cycle. Previous investigations confirm the assumption that the differing behaviour of the cell cycle machinery is controlled by the amount of mos protein.

Various oncoproteins such as the src and abl protein tyrosine kinases are likewise phosphorylated by the serinelthreonine kinase p34cdc2 in the context of mitosis. In the src family, mitotic phosphorylation is accompanied by increased kinase activity. The products of the tumour suppressor genes RB and p53 likewise form complexes with cyclin-p34cdc2 and are phosphorylated in this process. In the case of RB, the phosphorylation appears to be necessary in order to inactivate the RB function so that the cells of G1 can progress into the S phase. As a consequence of the aberrant expression of the cyclin-p34cdc2 complex, it follows that such tumour suppressor gene products are preserved in their phosphorylated inactive state, which results in unchecked cell division.

The connection between the function of serine/threonine kinases of the cell cycle and the transformation shows clearly that slight disturbances in the mitosis processes play a critical part in carcinogenesis. As carcinogenesis appears to be a multi-stage process, mutations in cell cycle regulators cooperate with mutations which activate protooncogenes or inactivate tumour suppressor genes.

On account of the enormous clinical importance of serine threonine kinases, there was thus a need to make available a new serine threonine kinase and the gene coding therefor.

The invention thus relates to a new serine threonine kinase called PLK, which is characterized in that it (a) comprises the amino acid sequence shown in SEQ ID No: 2 or (b) variants of the sequence from (a).

Preferably, the PLK protein according to the invention is a protein obtainable from man, i.e. it is the protein shown in SEQ ID No. 1 and No. 2 or a naturally occurring human variant thereof.

The invention also relates to a new protein which comprises parts of the amino acid sequence shown in SEQ ID No: 1 and 2. The invention preferably relates to a PLK protein which contains the amino acid sequence shown in SEQ ID No: 1 and 2; however, it can also contain variants of this sequence. The term "variants" within the meaning of the present invention is understood as meaning sequences which differ as a result of substitution, deletion and/or insertion of individual amino acids or short amino acid sections from the amino acid sequence shown in SEQ ID No: 1 and 2.

The term "variants" includes both naturally occurring allelic variations of the PLK protein, as well as proteins produced by recombinant DNA technology (in particular by in vitro mutagenesis with the aid of chemically synthesized oligonucleotides), which (correspond with respect to their biological and/or immunological activity to the protein shown in SEQ ID No: 1.

Proteins according to the invention are preferably distinguished in that on the amino acid level they have a homology of at least 95%, compared with the amino acid sequence shown in SEQ ID No: 1 and 2.

The gene PLK (polo-like kinase) described here and coding for the protein according to the invention was isolated from a cDNA bank, based on human lung tumour RNA (squamous cell carcinoma).

Expression of the PLK Gene in Proliferating Cells and Tissues

For a Northern blot investigation, RNA was isolated from the following human adult tissues: lung, liver, heart, brain, pancreas, kidney, placenta, skeletal muscle, oesophagus, colon, stomach and spleen. Only in placenta and colon, i.e. in tissues which contain a greater percentage of proliferating cells, was PLK expression detected. The length of the PLK-mRNA is about 2.3 kb. In the following, the hypothesis was investigated that PLK expression correlates with the proliferation of cells: for this, human tumours including surrounding normal reference tissue were investigated. Strong expression was found in tumours of the following organs: lung, breasts, oesophagus, stomach and intestine as well as in leiomyosarcomas and non-Hodgkin lymphornas. In a random sample group of 48 lung tumours, PLK was strongly expressed in 84% of the samples. In the remaining 16% of the tumours, PLK was expressed slightly or not at all. Southern blot investigations of restricted DNA from turnours and healthy reference tissues showed no differences with a PLK-specific sample.

Table 1 gives a breakdown by means of the tumour type and the PLK expression status:

TABLE 1

| | positive | negative |
|---|---|---|
| Lung: | | |
| Squamous cell carcinoma: | 24 | 2 |
| Adenocarcinoma: | 10 | 2 |
| Large-cell carcinoma: | 6 | 1 |
| Small-cell carcinoma: | 3 | 0 |
| References (adult human lung): | 0 | 48 |
| Liver metastasis: | 1 | 0 |
| Leiomyosarcoma: | 1 | 0 |
| Non-Hodgkin lymphoma: | 1 | 0 |
| Breast: | | |
| Breast carcinoma: | 7 | 1 |
| References (normal breast tissue): | 0 | 8 |
| Intestine: | | |
| Colorectal carcinoma: | 3 | 0 |
| References (normal colon tissue): | 3 | 0 |

In addition to human tissues and primary cells, the following cell lines were tested for PLK expression:
HELA cell line (cell type: cervix carcinoma),
lung epithelium cell line (cell type: lung carcinoma),
A431 cell line (cell type: epidermoid carcinoma),
HEP-38 cell line (cell type: hepatocellular carcinoma),
A498 cell line (cell type: kidney carcinoma),
BT 20 cell line (cell type: breast carcinoma),
T47D cell line (cell type: ductal breast carcinoma),
SKBR3 cell line (cell type: adenocarcinoma of the breast),
NCF7 cell line (cell type: adenocarcinoma of the breast) and
HUV-EC-C cell line (cell type: umbilical cord vein endothelial cells).

PLK transcripts were detectable in all cell lines investigated.

It was found that the expression of the PLK gene correlates with the proliferation activity. The possibility thus results of employing the amount of PLK gene products (mRNA or protein) as a measure of the division activity of a cell and thus as a proliferation marker for the analysis of human neoplasias. As emerges from Table 1, an increased PLK expression is detectable in a very high percentage of the tumours investigated. PLK is thus a universally employable proliferation marker.

Mitogen-induced Expression of PLK in Lymphocytes

Resting lymphocytes from peripheral blood do not express the PLK gene. Addition of PHA (phytohaemaglutinin) or PHA/IL-2 (interleukin-2) stimulates lymphocytes and the expression of PLK is induced. The expression of PLK can therefore also be taken as a measure of the activation of lymphocytes. In a further experiment, the cell line A431 was first cultured in serum-containing and then in serun free medium. The expression of PLK decreased in the course of the 5 days without serum After addition of serum, PLK expression increased strongly again.

Decrease of PLK Expression in Human Macrophages

Macrophages from peripheral blood are cells having, if at all, very low proliferation activity. Depending on the donor, macrophages after 15 days in culture had no or only very low PLK expression. After addition of LPS (lipopolysaccharide), the PLK (expression was switched off completely within 24 hours.

Correlation of PLK Expression with the Prognosis of Tumour Patients

It was furthermore found that the prognosis, in particular the life expectancy of tumour patients, correlates with the expression of PLK. For this, a relatively large collective of lung tumour patients was investigated and it was found that with increasing PLK expression the life expectancy of the patients falls. PLK can thus also be employed as a diagnostic tumour marker for the prognosis. The special feature of PLK can be seen in the fact that an increased expression occurs in more than 80% of the patients investigated, so that PLK is a very good tumour marker which indicates the presence of tumours with high probability.

The capability of PLK to be employed as a prognosis marker applies not only to lung tumours, but also to other tumours such as breast cancer, etc.

The invention thus relates to a process for the determination of the mitotic activity of cells, in particular of human cells, in which the expression potency of the gene coding for the PLK protein is determined in the cell concerned, e.g. on the transcription plane by Northern blot processes and/or on the protein plane by activity determinations or immunological methods. On account of the correlation of the PLK expression shown above in human tissues, primary cells and cell lines with the mitotic activity of the cells, the expression potency of the PLK gene represents a suitable variable in order to determine the status of specific cells with respect to mitotic activity. This process, which can be carried out extracorporeally, can be of great use, for example, in the field of tumour diagnosis or immunodiagnosis.

The amino acid sequence shown in SEQ ID No: 1 and 2 represents the total PLK protein. This protein has 603 amino acids. The PLK gene or variants thereof can be cloned routinely in a vector, such that this vector is brought into a suitable host cell for expression, the protein according to the invention being formed. Preferred host cells are microorganisms such as *E. coli* or yeast, but also higher cells (e.g. mammalian or insect cells). Preferred expression vectors are, for example, plasmids, bacteriophage lambda for prokaryotes, yeast vectors or viral vectors for higher cells (e.g. SV40, Vaccinia, Baculoviruses). With respect to the expression of the PLK gene, reference should be made in particular to the methods mentioned in Sambrook et al., (Molecular Cloning, A Laboratory Manual (1989) Cold Spring Harbor Laboratory Press). Furthermore, the expression of related kinase proteins is described in the works of Crews, C. M. et al., (1991), Proc. Natl. Acad. Sci. USA 88, 8845–8849; Ben-David, Y. et al., (1991) EMBO J. 10 (2), 317–325; Parker, L. L. et al., (1991) EMBO J. 10 (5), 1255–1263; Parker L. L. et al., (1992) Science 257, 1955–1957; Colemamn, T. R. et al., (1993) Cell 72, 919–929, to whose disclosure reference is made here for this purpose.

A comparison of the PLK sequence with the EMBL databank yields a high measure of homology with the family of serine(threonine kinases. The protein according to the invention is called PLK (polo-like kinase) on account of its homology to the polo gene, which was isolated from Drosophila melanogaster.

The following protein kinase-specific sequence characteristics occur:

1. The ATP binding pattern:
   GlyLysGlyGlyPheAla . . . (16 amino acids) . . . Lys (amino acids 60–86) as shown in SEQ ID No: 2
2. Two amino acid patterns lying in the catalytic domain of protein kinases, which are highly conserved in all protein kinases with respect to the amino acid sequence and the distance of the patterns from one another:
   HisArgAspLeu (AA 174–177) as shown in SEQ ID No: 2
   AspPheGly (AA 194–196) as shown in SEQ ID No: 2

The present invention furthermore relates to a nucleic acid which codes for a PLK protein according to the invention or parts thereof. This nucleic acid can be, for (example, genomic DNA or RNA Preferably, however, it is in this case a recombinant DNA molecule.

The invention furthermore relates to a nucleic acid according to the invention, which (a) contains the coding sequence shown in SEQ ID No: 1, (b) a nucleic acid sequence corresponding to the sequence from (a) in the context of the degeneration of the genetic code or (c) a sequence hybridizer with the sequences from (a) and/or (b) under stringent hybridization conditions.

Under stringent hybridization conditions within the meaning of the present invention is understood as meaning that a hybridization still occurs even after washing at 55° C., preferaly at 62° C., particularly preferably at 68° C., in an aqueous low-salt buffer (e.g. 0.2×SSC, 0.1% SDS) (see also Sambrook, J. et al., (1989), Molecular Cloning. A Laboratory Manual).

The invention also relates to nucleic acids which contain a section at least 20 nucleotides long of the sequence shown in SEQ ID No.: 1. Preferably, this section has a nucleotide sequence specific for the PLK gene. These nucleic acids are suitable, in particular, for the production of antisense nucleic acids which can be employed therapeutically.

Additionally, the invention further relates to a vector which contains at least one copy of a nucleic acid according to the invention or a part thereof. The vector can be replicable in eukaryotes or prokaryotes. It can be a vector which can be integrated into the genome of the host cell (e.g. bacteriophage lambda) or a vector which is present extrachromosomally (e.g. a plasmid). The vector according to the invention can be obtained by subcloning of the PLK gene in a base vector. Base vectors of this type, in particular vectors containing the elements necessary for protein expression, are familiar to a person skilled in the art.

The present invention further relates to a cell which is transformed using a nucleic acid according to the invention or a vector according to the invention. The cell can be either a eukaryotic or a prokaryotic cell. Processes for the transformation of cells are general prior art and therefore do not need to be explained.

The present invention likewise relates to the use of the PLK protein or of the gene coding therefor or of an antibody directed against the protein in tumour diagnosis. Experiments have shown that the expression of the PLK gene in tumours and corresponding tumour-free reference tissues is different. There is therefore the possibility to draw conclusions on the mitotic activity of cells from the level of expression of the gene or of the protein.

The invention additionally relates to a diagnostic or therapeutic composition based on a PLK protein, on an antibody directed against it or a nucleic acid according to the invention (e.g. as an antisense nucleic acid for the suppression of gene expression). A composition of this type can optionally contain known pharmaceutical diluents, fillers, excipients and auxiliaries.

It was possible to show the inhibition of the growth of cells by inhibition of PLK expression experimentally by antisense constructs and by dominant-negative mutants. A particularly preferred aspect of the present invention is therefore the gene therapy application of the nucleic acids according to the invention, in which these nucleic acids are administered to a patient in replicable form (e.g. on a vector suitable for integration into the genome), e.g. in order to produce antisense nucleic acids within the cell. Alternatively, the antisense nucleic acids can also be introduced directly into the cell (e.g. by microinjection).

The invention further relates to a method for the determination of the activity of lymphocytes, in which a protein according to the invention, a nucleic acid according to the invention or an antibody directed against the protein is used. This method can be carried out, for example, extracorporeally on taken blood samples. This process is particularly suitable for the detection of disorders of the immune system, in particular in autoimmune disorders or immunodeficiency syndromes including AIDS.

Finally, the present invention additionally comprises the use of the PLK protein or of fragments of this protein as an immunogen for the production of antibodies. The production of antibodies against the PLK protein is carried out in a customary manner by immunization of experimental animals with the complete PLK protein or fragments thereof and subsequent recovery of the resulting (polyclonal) antibodies. According to the method of Köhler and Milstein or its further developments, monoclonal antibodies can be obtained from the PLK antibody-producing cells of the experimental animals in a known manner by cell fusion. Human monoclonal antibodies can also be obtained.

SEQ ID No. 7 shows a nucleic acid sequence 2503 bp long, which contains the region attaching directly to the 5'-side on the start codon of the PLK gene. It was possible to detect by chloramphenicol transferase (CAT) assays, that the indicated sequence includes the promoter of the PLK gene. The starting point of the transcription in SEQ ID No: 7 is at nucleotide 2460. Positive-regulatory elements of the promoter are found within the regions between the nucleotides 184 and 676, and 1163 and 2503. Negative-regulatory elements are found within the region between the nucleotides 676 and 1163. It was possible to idenify these regulatory elements with the aid of CAT assays using deletion clones. By sequence comparison, it was furthermore found that a CCAAT box is localized between the nucleotides 2407 and 2411 and two potential SP1 binding sites are localized between the nucleotides 2375–2384.

The PLK promoter has the property that it is only active in proliferating cells. It can therefore also be employed in combination with a gene which is toxic for the cells (e.g. the gene for diphtheria toxin or the gene for cholera toxin) for the gene therapy treatment of tumours. The PLK promoter in combination with the PLK gene in the antisense orientation offers a further possibility of therapeutic use. In this manner, a selective inhibition of the growth of dividing cells can be achieved The present invention thus also relates to a nucleic acid which contains the sequence shown in SEQ ID No: 7 or a section thereof, preferably a section having identical biological activity. This nucleic acid can be, for example, in operative linkage with a toxic gene or with the PLK gene in the antisense orientation or a section thereof which is preferably longer than 20 nucleotides. These nucleic acids can be used, in particular, for gene therapy.

The invention is intended to be explained further by the sequence protocol and figure SEQ ID No: 1 to SEQ ID No: 7 and FIG. 1 together with following examples, without it being intended here to restrict the scope of the invention.

SEQ ID No: 1 shows a 2124 bp-long nucleic acid sequence, which contains the genetic information coding for the PLK gene, SEQ ID No: 2 shows the 603 AA-long amino acid sequence of the PLK protein, SEQ ID No: 3 shows the nucleic acid sequence of the oligonucleotide primer P6 DEA SEQ ID No: 4 shows the nucleic acid sequence of the oligonucleotide primer Eco HRDL SEQ ID No: 5 shows the nucleic acid sequence of the oligonucleotide primer P12T+, SEQ ID No: 6 shows the nucleic acid sequence of the oligonucleotide primer RAF2 and SEQ ID No: 7 shows the 2503 bp-long nucleic acid sequence of the PLK promoter

EXAMPLE 1

Figure 1:
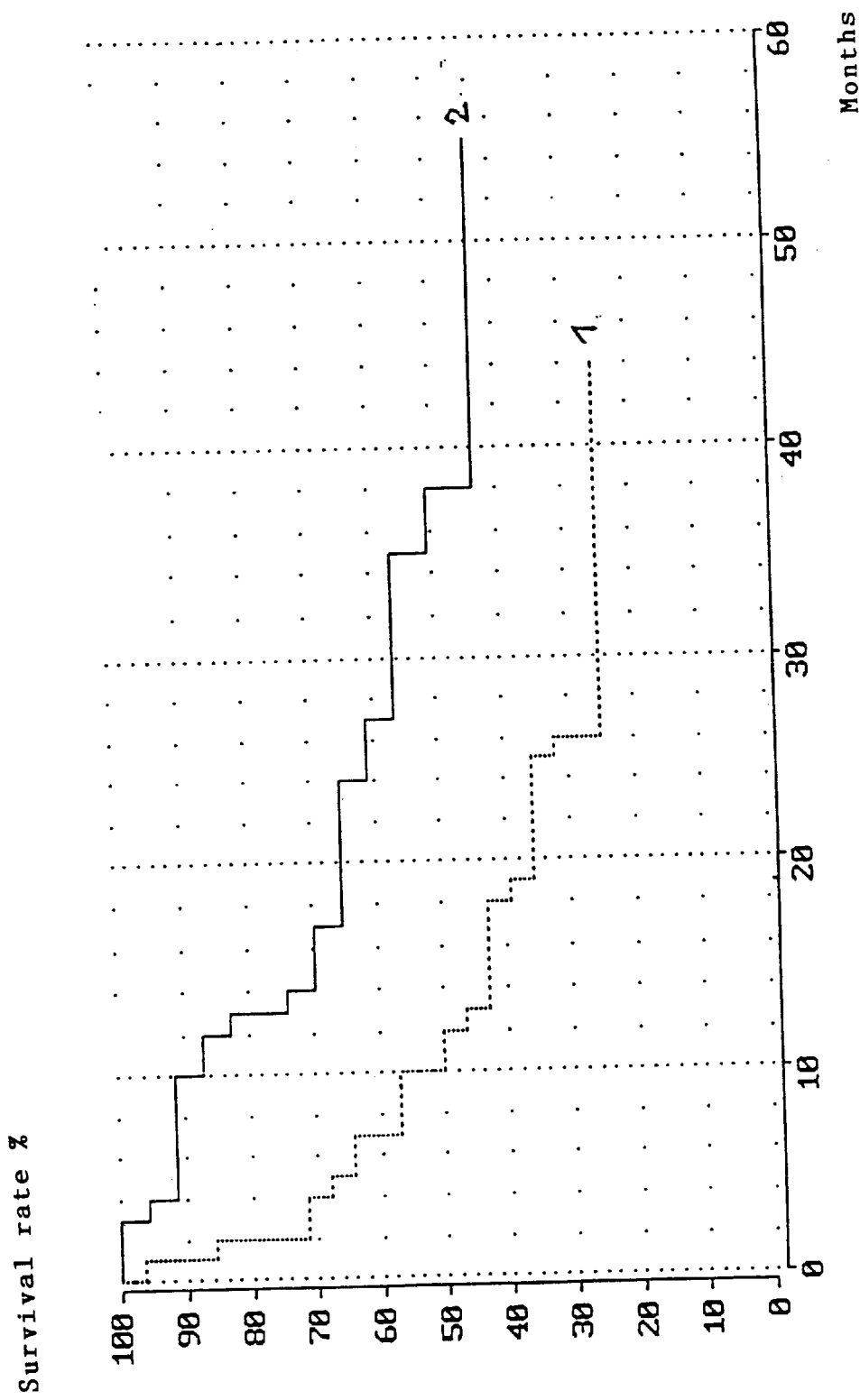
FIG. 1 shows the post-operative survival rate of lung cancer patients as a function of PLK expression.

Isolation of a part sequence of the PLK gene
1.1 RNA was isolated from human lung tumour tissue according to the method of Chirgwin et al., (Biochemistry 18 (1979), 5294). Using this RNA, an oligo(dT)-mediated cDNA synthesis was carried out. The reaction conditions were as follows:

50 mmol/l of tris/HCl, pH 8.3 (22° C.)
75 mmol/l of KCl
10 mmol/l of dithiothreitol (DTT)
3 mmol/l of $MgCl_2$
500 μmol/l of dNTP solution
0.2 μmol/l of oligonucleotide primer P12T+ having the nucleic acid sequence shown in SEQ ID No: 5
3.0 μg of total RNA
100 μg/ml of bovine serum albumin
10 units of reverse transcriptase (from Moloney murine leukemia virus)

The above reaction mixture was incubated at 37° C. for one hour in a reaction volume of 20 μl.

1.2 The cDNA from 1.1 was amplified using two primers Eco HRDL and P6 DEA complementary to two too-highly conserved regions of PTK genes. The nucleic acid sequence of the primer P6 DEA is indicated in SEQ ID No: 3. The sequence of Eco HRDL is shown in SEQ ID No: 4 (this sequence is homologous to the nucleotides 588 to 601 of the sequence shown in SEQ ID No: 1).

Reaction conditions:
8.3 mmol/l of tris/HCl, pH 8.8 (22° C.)
41.7 mmol/l of KCl
1.25 mmol/l of $MgCl_2$
0.01% of gelatin
166.7 μmol/l of dNTP solution
0.6 μmol/l of primer P6 DEA and Eco HRDL
5 units of Taq polymerase
10 μl of cDNA synthesis mixture The reaction volume was 60 μl. The conditions for a PCR cycle were as follows:
95° C. denaturation for 1 minute,
40° C. hybridization for 2 minutes,
72° C. elongation for 3 minutes.
A total of 40 cycles were carried out.

The amplificate formed was separated electrophoretically in a 2% strength agarose gel for the purpose of purification and the DNA in the length region from about 190 bp to 220 bp was electrically eluted and amplified again for 30 cycles under the conditions indicated above. The PCR products thus obtained and purified were then digested using the restriction endonuclease EcoRI and cloned into the Bluescript-KS vector (Stratagene) which was likewise cleaved with EcoRI.

In this manner, a 199 bp-long DNA fragment was isolated and sequenced (Sambrook J. et al., Molecular Cloning, A Laboratory Manual, Cold Spring Harbor Laboratory 1989). The nucleic acid sequence of this DNA fragment corresponds to the nucleotides 588 to 787 of the sequence shown in SEQ ID No: 1.

EXAMPLE 2

Isolation of a PLK-cDNA

A cDNA bank from poly A+ RNA of human lung tumour tissue was established using $1.8 \times 10^6$ recombinant clones. The isolation of the mRNA was carried out according to Aviv and Leder (Proc. Natl. Acad. Sci. USA 69 (1972), 1408). The cDNA cloning was carried out according to Gubler and Hoffinan (Gene 25 (1983), 263). This gene bank was inspected by means of a DNA probe. The DNA probe was prepared by PCR. The oligonucleotide RAF2 was used as a primer for the PCR. The nucleic acid sequence for RAF2 is shown in SEQ ID No: 6 (this sequence corresponds to the nucleotides 746 to 767 of the sequence shown in SEQ ID No: 1).

Reaction conditions:
20 ng of PLK insert (from Example 1)
10 mmol/l of tris/HCl, pH 8.8 (22° C.)
50 mmol/l of KCl
1.5 mmol/l of MgCl$_2$
0.01% of gelatin
0.8 µmmol/l of α$^{32}$P-dCTP (6000 Ci/mmol)
0.8 µmmol/l of dATP/dGTP/dTTP
0.2 µmmol/l of the primer RAF2
2.5 units of Taq polymerase The reaction volume was 25 µl. The reaction was carried out in 20 cycles under the PCR conditions mentioned above (in Example 1).

For the detection of a positive clone, cDNA from the gene bank was immobilized on filters and hybridize on the radiolabelled DNA probe (1×10$^6$ dpm/ml of solution at a specific probe activity of 5×10$^9$ dpm/µg of DNA). The hybridization temperature was 42° C.

Hybridization solution:
5×SSC
0.02 mol/l of tris/HCl, pH 7.6 (22° C.)
1×Denhardt solution
10% of dextan sulphate
0.1% of SDS
100 µg/ml of herring sperm DNA
50% of formamide The washing solution employed was 2×SSC, 0.1% SDS at a washing temperature of 42° C.

A positive clone was found and characterized. It contained the nucleic acid sequence shown in SEQ ID No: 1.

EXAMPLE 3

Inhibition of PLK expression

1×10$^4$ A431 cells were seeded and allowed to grow for 2 to 3 days to a confluence of 95%. The culture was then kept for 24 hours in RPMI 1640 medium containing 0.5% foetal calf serum 1 to 2×10$^{-12}$ ml of a liquid containing 2 µg/µl of TKF antisense RNA per cell were injected by microinjection. This TKF antisense RNA was prepared using T3 or T7 RNA polymerase by transcription of the sequence shown in SEQ ID No: 1 in reverse orientation.

The cells were kept further in RPMI 1640 medium containing 0.5% or 10% foetal calf serum. After 18 hours, the cells were pulsed with $^3$H-thymidine (0.5 µCi/ml; Amersham) for 3 to 4 hours. After washing with phosphate-buffered saline solution (PBS), fixing was carried out in 3.5% formaldehyde-PBS, then layering with film emulsion (NTP-2, Kodak) and incubation for 48 hours for the purpose of development. The cells were stained according to Giemsa, counted and photographed. It was shown that it was possible to inhibit the PLK expression and the growth of cells by addition of the antisense RNA.

EXAMPLE 4

PLK as a diagnostic tumour marker

It was found that in operated lung tumour patients there is a clear correlation of PLK expression with the survival time of the patient. It was found that patients with high PLK expression die significantly earlier than those in the comparison group having low PLK expression.

The results of this experiment are indicated in the following Table 2. For the analysis of PLK expression, the mRNA from the tumour tissue of the respective patient was investigated by means of a Northern blot analysis. The values indicated in Table 2 are standardized with respect to the expression of actin mRNA. The survival time of the patients after the operation is indicated in months. The symbol "*" means that the patient was still alive at the time indicated.

TABLE 2

| Patient No. | Age/sex | Tumour stage | Tumour | Post-operative survival time | PLK expression |
|---|---|---|---|---|---|
| 1 | 71 m | II | Squamous cell carcinoma | 10 | 3.79 |
| 2 | 71 m | III | | *28 | 0.48 |
| 3 | 60 m | III | | 5 | 1.02 |
| 4 | 54 m | III | | 19 | 1.12 |
| 5 | 61 m | I | | 17 | 0.36 |
| 6 | 67 m | ? | | 24 | 0.15 |
| 7 | 70 m | I | | 35 | 0.90 |
| 8 | 69 m | II | | *41 | 0.08 |
| 9 | 72 m | I | | *37 | 0.67 |
| 10 | 67 m | III | | *55 | 0.35 |
| 11 | 66 m | II | | 10 | 0.13 |
| 12 | 57 m | I | | *31 | 0.10 |
| 13 | 61 m | I | | 4 | 6.94 |
| 14 | 64 m | I | | 7 | 1.96 |
| 15 | 42 m | II | | 27 | 0.28 |
| 16 | 70 m | I | | 0 | 3.84 |
| 17 | 54 m | II | | 25 | 4.66 |
| 18 | 61 m | II | | 12 | 1.99 |
| 19 | 67 m | I | | 7 | 1.14 |
| 20 | 70 m | II | | 0 | 3.75 |
| 21 | 53 f | I | | *38 | 1.41 |
| 22 | 36 m | II | | *37 | 8.57 |
| 23 | 75 m | I | | 4 | 2.01 |
| 24 | 77 f | I | Adenocarcinoma | *38 | 0.31 |
| 25 | 56 m | II | | *32 | 0.73 |
| 26 | 56 m | III | | 13 | 2.14 |
| 27 | 71 m | III | | 2 | 13.1 |
| 28 | 72 m | I | | *32 | 1.04 |
| 29 | 54 m | III | | 14 | 0.94 |
| 30 | 60 m | I | | 26 | 1.34 |
| 31 | 70 m | I | | 38 | 0.96 |
| 32 | 43 m | I | | *32 | 4.12 |
| 33 | 62 m | III | Large-cell carcinoma | 26 | 3.97 |
| 34 | 66 m | I | | *44 | 14.8 |
| 35 | 66 f | III | | 2 | 32.3 |
| 36 | 64 m | I | | 2 | 11.0 |
| 37 | 40 m | I | | *36 | 17.9 |
| 38 | 53 f | III | | 0 | 5.50 |
| 39 | 61 m | I | Mixed-cell carcinoma | 4 | 0.10 |
| 40 | 57 m | II | | 0 | 3.34 |
| 41 | 49 m | I | | 3 | 0.33 |
| 42 | 76 f | I | Broncheoalveolar carcinoma | *43 | 0.40 |
| 43 | 77 f | I | | *44 | 0.12 |
| 44 | 77 f | II | | *48 | 0.02 |
| 45 | 57 m | | | *42 | 0.12 |
| 46 | 77 m | III | Small-cell lung cancer | 13 | 0.55 |
| 47 | 62 m | I | | 10 | 6.23 |
| 48 | 63 m | III | | 18 | 11.2 |
| 49 | 58 m | I | | *35 | 11.2 |
| 50 | 63 m | II | | 13 | 0.04 |
| 51 | 46 m | III | Leiomyosarcoma in the lung | 12 | 0.42 |

FIG. 1 shows the associated statistical Kaplan-Meier assessment of the patient data (E. L. Kaplan and P. Meier, J. Am. Stat. Assoc. 53 (1958), 457–481). Curve 1 shows the post-operative survival rate of 23 lung cancer patients with an absolute PLK expression>1 (standardized on actin). Curve 2 shows the survival rate of 28 lung cancer patients having an absolute standardized PLK expression<1. It is evident from FIG. 1 that patients having high PLK expression die significantly earlier than those in the comparison group having low PLK expression.

(1) GENERAL INFORMATION:

(iii) NUMBER OF SEQUENCES: 7

(2) INFORMATION FOR SEQ ID NO: 1:

(i) SEQUENCE CHARACTERISTICS:
       (A) LENGTH: 2124 base pairs
       (B) TYPE: nucleic acid
       (C) STRANDEDNESS: both
       (D) TOPOLOGY: linear (ii) MOLECULE TYPE: cDNA (iii) ANTI-SENSE: yes (vi) ORIGINAL SOURCE:
       (A) ORGANISM: Homo sapiens (ix) FEATURE:
       (A) NAME/KEY: CDS
       (B) LOCATION: 65..1873

(xi) SEQUENCE DESCRIPTION: SEQ ID NO: 1:

```
GGGGAGGAGC GGAGCGGTGC GGAGGCTCTG CTCGGATCGA GGTCTGCAGC GCAGCTTCGG        60

GAGC ATG AGT GCT GCA GTG ACT GCA GGG AAG CTG GCA CGG GCA          103
           Met Ser Ala Ala Val Thr Ala Gly Lys Leu Ala Arg Ala
             1               5                  10

CCG GCC GAC CCT GGG AAA GCC GGG GTC CCC GGA GTT GCA GCT CCC GGA         151
Pro Ala Asp Pro Gly Lys Ala Gly Val Pro Gly Val Ala Ala Pro Gly
 15              20                  25

GCT CCG GCG GCG GCT CCA CCG GCG AAA GAG ATC CCG GAG GTC CTA GTG         199
Ala Pro Ala Ala Ala Pro Pro Ala Lys Glu Ile Pro Glu Val Leu Val
 30              35                  40                      45

GAC CCA CGC AGC CGG CGG CGC TAT GTG CGG GGC CGC TTT TTG GGC AAG         247
Asp Pro Arg Ser Arg Arg Arg Tyr Val Arg Gly Arg Phe Leu Gly Lys
             50                  55                  60

GGC GGC TTT GCC AAG TGC TTC GAG ATC TCG GAC GCG GAC ACC AAG GAG         295
Gly Gly Phe Ala Lys Cys Phe Glu Ile Ser Asp Ala Asp Thr Lys Glu
             65                  70                  75

GTG TTC GCG GGC AAG ATT GTG CCT AAG TCT CTG CTG CTC AAG CCG CAC         343
Val Phe Ala Gly Lys Ile Val Pro Lys Ser Leu Leu Leu Lys Pro His
             80                  85                  90

CAG AGG GAG AAG ATG TCC ATG GAA ATA TCC ATT CAC CGC AGC CTC GCC         391
Gln Arg Glu Lys Met Ser Met Glu Ile Ser Ile His Arg Ser Leu Ala
 95                  100                 105

CAC CAG CAC GTC GTA GGA TTC CAC GGC TTT TTC GAG GAC AAC GAC TTC         439
His Gln His Val Val Gly Phe His Gly Phe Phe Glu Asp Asn Asp Phe
110                 115                 120                 125

GTG TTC GTG GTG TTG GAG CTC TGC CGC CGG AGG TCT CTC CTG GAG CCG         487
Val Phe Val Val Leu Glu Leu Cys Arg Arg Arg Ser Leu Leu Glu Pro
                130                 135                 140

CAC AAG AGG AGG AAA GCC CTG ACT GAG CCT GAG GCC CGA TAC TAC CTA         535
His Lys Arg Arg Lys Ala Leu Thr Glu Pro Glu Ala Arg Tyr Tyr Leu
                145                 150                 155

CGG CAA ATT GTG CTT GGC TGC CAG TAC CTG CAC CGA AAC CGA GTT ATT         583
Arg Gln Ile Val Leu Gly Cys Gln Tyr Leu His Arg Asn Arg Val Ile
                160                 165                 170

CAT CGA GAC CTC AAG CTG GGC AAC CTT TTC CTG AAT GAA GAT CTG GAG         631
His Arg Asp Leu Lys Leu Gly Asn Leu Phe Leu Asn Glu Asp Leu Glu
            175                 180                 185
```

```
                                                                -continued

GTG AAA ATA GGG GAT TTT GGA CTG GCA ACC AAA GTC GAA TAT GAC GGG      679
Val Lys Ile Gly Asp Phe Gly Leu Ala Thr Lys Val Glu Tyr Asp Gly
190             195                 200                 205

GAG AGG AAG AAG ACC CTG TGT GGG ACT CCT AAT TAC ATA GCT CCC GAG      727
Glu Arg Lys Lys Thr Leu Cys Gly Thr Pro Asn Tyr Ile Ala Pro Glu
                210                 215                 220

GTG CTG AGC AAG AAA GAG CAC AGT TTC GAG GTG GAT GTG TGG TCC ATT      775
Val Leu Ser Lys Lys Glu His Ser Phe Glu Val Asp Val Trp Ser Ile
                225                 230                 235

GGG TGT ATC ATG TAT ACC TTG TTA GTG GGC AAA CCA CCT TTT GAG ACT      823
Gly Cys Ile Met Tyr Thr Leu Leu Val Gly Lys Pro Pro Phe Glu Thr
                240                 245                 250

TCT TGC CTA AAA GAG ACC TAC CTC CGG ATC AAG AAG AAT GAA TAC AGT      871
Ser Cys Leu Lys Glu Thr Tyr Leu Arg Ile Lys Lys Asn Glu Tyr Ser
255                 260                 265

ATT CCC AAG CAC ATC AAC CCC GTG GCC GCC TCC CTC ATC CAG AAG ATG      919
Ile Pro Lys His Ile Asn Pro Val Ala Ala Ser Leu Ile Gln Lys Met
270                 275                 280                 285

CTT CAG ACA GAT CCC ACT GCC CGC CCA ACC ATT AAC GAG CTG CTT AAT      967
Leu Gln Thr Asp Pro Thr Ala Arg Pro Thr Ile Asn Glu Leu Leu Asn
                290                 295                 300

GAC GAG TTC TTT ACT TCT GGC TAT ATC CCT GCC CGT CTC CCC ATC ACC     1015
Asp Glu Phe Phe Thr Ser Gly Tyr Ile Pro Ala Arg Leu Pro Ile Thr
                305                 310                 315

TGC CTG ACC ATT CCA CCA AGG TTT TCG ATT GCT CCC AGC AGC CTG GAC     1063
Cys Leu Thr Ile Pro Pro Arg Phe Ser Ile Ala Pro Ser Ser Leu Asp
                320                 325                 330

CCC AGC AAC CGG AAG CCC CTC ACA GTC CTC AAT AAA GGC TTG GAG AAC     1111
Pro Ser Asn Arg Lys Pro Leu Thr Val Leu Asn Lys Gly Leu Glu Asn
335                 340                 345

CCC CTG CCT GAG CGT CCC CGG GAA AAA GAA GAA CCA GTG GTT CGA GAG     1159
Pro Leu Pro Glu Arg Pro Arg Glu Lys Glu Glu Pro Val Val Arg Glu
350                 355                 360                 365

ACA GGT GAG GTG GTC GAC TGC CAC CTC AGT GAC ATG CTG CAG CAG CTG     1207
Thr Gly Glu Val Val Asp Cys His Leu Ser Asp Met Leu Gln Gln Leu
                370                 375                 380

CAC AGT GTC AAT GCC TCC AAG CCC TCG GAG CGT GGG CTG GTC AGG CAA     1255
His Ser Val Asn Ala Ser Lys Pro Ser Glu Arg Gly Leu Val Arg Gln
                385                 390                 395

GAG GAG GCT GAG GAT CCT GCC TGC ATC CCC ATC TTC TGG GTC AGC AAG     1303
Glu Glu Ala Glu Asp Pro Ala Cys Ile Pro Ile Phe Trp Val Ser Lys
                400                 405                 410

TGG GTG GAC TAT TCG GAC AAG TAC GGC CTT GGG TAT CAG CTC TGT GAT     1351
Trp Val Asp Tyr Ser Asp Lys Tyr Gly Leu Gly Tyr Gln Leu Cys Asp
415                 420                 425

AAC AGC GTG GGG GTG CTC TTC AAT GAC TCA ACA CGC CTC ATC CTC TAC     1399
Asn Ser Val Gly Val Leu Phe Asn Asp Ser Thr Arg Leu Ile Leu Tyr
430                 435                 440                 445

AAT GAT GGT GAC AGC CTG CAG TAC ATA GAG CGT GAC GGC ACT GAG TCC     1447
Asn Asp Gly Asp Ser Leu Gln Tyr Ile Glu Arg Asp Gly Thr Glu Ser
                450                 455                 460

TAC CTC ACC GTG AGT TCC CAT CCC AAC TCC TTG ATG AAG AAG ATC ACC     1495
Tyr Leu Thr Val Ser Ser His Pro Asn Ser Leu Met Lys Lys Ile Thr
                465                 470                 475

CTC CTT AAA TAT TTC CGC AAT TAC ATG AGC GAG CAC TTG CTG AAG GCA     1543
Leu Leu Lys Tyr Phe Arg Asn Tyr Met Ser Glu His Leu Leu Lys Ala
                480                 485                 490

GGT GCC AAC ATC ACG CCG CGC GAA GGT GAT GAG CTC GCC CGG CTG CCC     1591
Gly Ala Asn Ile Thr Pro Arg Glu Gly Asp Glu Leu Ala Arg Leu Pro
495                 500                 505
```

-continued

```
TAC CTA CGG ACC TGG TTC CGC ACC CGC AGC GCC ATC ATC CTG CAC CTC    1639
Tyr Leu Arg Thr Trp Phe Arg Thr Arg Ser Ala Ile Ile Leu His Leu
510                 515                 520                 525

AGC AAC GGC AGC GTG CAG ATC AAC TTC TTC CAG GAT CAC ACC AAG CTC    1687
Ser Asn Gly Ser Val Gln Ile Asn Phe Phe Gln Asp His Thr Lys Leu
                530                 535                 540

ATC TTG TGC CCA CTG ATG GCA GCC GTG ACC TAC ATC GAC GAG AAG CGG    1735
Ile Leu Cys Pro Leu Met Ala Ala Val Thr Tyr Ile Asp Glu Lys Arg
                    545                 550                 555

GAC TTC CGC ACA TAC CGC CTG AGT CTC CTG GAG GAG TAC GGC TGC TGC    1783
Asp Phe Arg Thr Tyr Arg Leu Ser Leu Leu Glu Glu Tyr Gly Cys Cys
                        560                 565                 570

AAG GAG CTG GCC AGC CGG CTC CGC TAC GCC CGC ACT ATG GTG GAC AAG    1831
Lys Glu Leu Ala Ser Arg Leu Arg Tyr Ala Arg Thr Met Val Asp Lys
575                 580                 585

CTG CTG AGC TCA CGC TCG GCC AGC AAC CGT CTC AAG GCC TCC            1873
Leu Leu Ser Ser Arg Ser Ala Ser Asn Arg Leu Lys Ala Ser
590                 595                 600

TAATAGCTGC CCTCCCCTCC GGACTGGTGC CCTCCTCACT CCCACCTGCA TCTGGGGCCC    1933

ATACTGGTTG GCTCCCGCGG TGCCATGTCT GCAGTGTGCC CCCCAGCCCC GGTGGCTGGG    1993

CAGAGCTGCA TCATCCTTGC AGGTGGGGGT TGCTGTATAA GTTATTTTTG TACATGTTCG    2053

GGTGTGGGTT CTACAGACTT GTCCCCCTCC CCCTCAACCC CACCATATGA ATTGTACAGA    2113

ATATTTCTAT T                                                         2124
```

(2) INFORMATION FOR SEQ ID NO: 2:

(i) SEQUENCE CHARACTERISTICS:
        (A) LENGTH: 603 amino acids
        (B) TYPE: amino acid
        (D) TOPOLOGY: linear (ii) MOLECULE TYPE: Protein (xi) SEQUENCE DESCRIPTION: SEQ ID NO: 2:

```
Met Ser Ala Ala Val Thr Ala Gly Lys Leu Ala Arg Ala Pro Ala Asp
1               5                   10                  15

Pro Gly Lys Ala Gly Val Pro Gly Val Ala Ala Pro Gly Ala Pro Ala
                20                  25                  30

Ala Ala Pro Pro Ala Lys Glu Ile Pro Glu Val Leu Val Asp Pro Arg
            35                  40                  45

Ser Arg Arg Arg Tyr Val Arg Gly Arg Phe Leu Gly Lys Gly Gly Phe
        50                  55                  60

Ala Lys Cys Phe Glu Ile Ser Asp Ala Asp Thr Lys Glu Val Phe Ala
65                  70                  75                  80

Gly Lys Ile Val Pro Lys Ser Leu Leu Leu Lys Pro His Gln Arg Glu
                85                  90                  95

Lys Met Ser Met Glu Ile Ser Ile His Arg Ser Leu Ala His Gln His
                100                 105                 110

Val Val Gly Phe His Gly Phe Phe Glu Asp Asn Asp Phe Val Phe Val
            115                 120                 125

Val Leu Glu Leu Cys Arg Arg Arg Ser Leu Leu Glu Pro His Lys Arg
        130                 135                 140

Arg Lys Ala Leu Thr Glu Pro Glu Ala Arg Tyr Tyr Leu Arg Gln Ile
145                 150                 155                 160

Val Leu Gly Cys Gln Tyr Leu His Arg Asn Arg Val Ile His Arg Asp
                165                 170                 175
```

```
Leu Lys Leu Gly Asn Leu Phe Leu Asn Glu Asp Leu Glu Val Lys Ile
            180                 185                 190
Gly Asp Phe Gly Leu Ala Thr Lys Val Glu Tyr Asp Gly Glu Arg Lys
            195                 200                 205
Lys Thr Leu Cys Gly Thr Pro Asn Tyr Ile Ala Pro Glu Val Leu Ser
            210                 215                 220
Lys Lys Glu His Ser Phe Glu Val Asp Val Trp Ser Ile Gly Cys Ile
225                 230                 235                 240
Met Tyr Thr Leu Leu Val Gly Lys Pro Pro Phe Glu Thr Ser Cys Leu
            245                 250                 255
Lys Glu Thr Tyr Leu Arg Ile Lys Lys Asn Glu Tyr Ser Ile Pro Lys
            260                 265                 270
His Ile Asn Pro Val Ala Ala Ser Leu Ile Gln Lys Met Leu Gln Thr
            275                 280                 285
Asp Pro Thr Ala Arg Pro Thr Ile Asn Glu Leu Leu Asn Asp Glu Phe
            290                 295                 300
Phe Thr Ser Gly Tyr Ile Pro Ala Arg Leu Pro Ile Thr Cys Leu Thr
305                 310                 315                 320
Ile Pro Pro Arg Phe Ser Ile Ala Pro Ser Ser Leu Asp Pro Ser Asn
            325                 330                 335
Arg Lys Pro Leu Thr Val Leu Asn Lys Gly Leu Glu Asn Pro Leu Pro
            340                 345                 350
Glu Arg Pro Arg Glu Lys Glu Glu Pro Val Val Arg Glu Thr Gly Glu
            355                 360                 365
Val Val Asp Cys His Leu Ser Asp Met Leu Gln Gln Leu His Ser Val
370                 375                 380
Asn Ala Ser Lys Pro Ser Glu Arg Gly Leu Val Arg Gln Glu Glu Ala
385                 390                 395                 400
Glu Asp Pro Ala Cys Ile Pro Ile Phe Trp Val Ser Lys Trp Val Asp
                405                 410                 415
Tyr Ser Asp Lys Tyr Gly Leu Gly Tyr Gln Leu Cys Asp Asn Ser Val
                420                 425                 430
Gly Val Leu Phe Asn Asp Ser Thr Arg Leu Ile Leu Tyr Asn Asp Gly
            435                 440                 445
Asp Ser Leu Gln Tyr Ile Glu Arg Asp Gly Thr Glu Ser Tyr Leu Thr
            450                 455                 460
Val Ser Ser His Pro Asn Ser Leu Met Lys Lys Ile Thr Leu Leu Lys
465                 470                 475                 480
Tyr Phe Arg Asn Tyr Met Ser Glu His Leu Leu Lys Ala Gly Ala Asn
                485                 490                 495
Ile Thr Pro Arg Glu Gly Asp Glu Leu Ala Arg Leu Pro Tyr Leu Arg
                500                 505                 510
Thr Trp Phe Arg Thr Arg Ser Ala Ile Ile Leu His Leu Ser Asn Gly
            515                 520                 525
Ser Val Gln Ile Asn Phe Phe Gln Asp His Thr Lys Leu Ile Leu Cys
            530                 535                 540
Pro Leu Met Ala Ala Val Thr Tyr Ile Asp Glu Lys Arg Asp Phe Arg
545                 550                 555                 560
Thr Tyr Arg Leu Ser Leu Leu Glu Glu Tyr Gly Cys Cys Lys Glu Leu
            565                 570                 575
Ala Ser Arg Leu Arg Tyr Ala Arg Thr Met Val Asp Lys Leu Leu Ser
            580                 585                 590
```

```
Ser Arg Ser Ala Ser Asn Arg Leu Lys Ala Ser
    595                 600
```

(2) INFORMATION FOR SEQ ID NO: 3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: yes (iii) ANTI-SENSE: no (xi) SEQUENCE DESCRIPTION: SEQ ID NO: 3:

```
TTGGAATTCA TCCCNNNNNN CCACACATC                              29
```

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: yes (iii) ANTI-SENSE: no (xi) SEQUENCE DESCRIPTION: SEQ ID NO: 4:

```
TTTGGAATTC GTNCAYMGNG AYYT                                   24
```

(2) INFORMATION FOR SEQ ID NO: 5:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: yes (iii) ANTI-SENSE: no (xi) SEQUENCE DESCRIPTION: SEQ ID NO: 5:

```
GCAGAATTCG TGAACTGCGG CCGCATTTTT TTTTTTT                     37
```

(2) INFORMATION FOR SEQ ID NO: 6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: yes (iii) ANTI-SENSE: no (xi) SEQUENCE DESCRIPTION: SEQ ID NO: 6:

```
CACCTCGAAA CTGTGCTCTT TC                                     22
```

(2) INFORMATION FOR SEQ ID NO: 7:

(i) SEQUENCE CHARACTERISTICS:
        (A) LENGTH: 2503 base pairs
        (B) TYPE: nucleic acid
        (C) STRANDEDNESS: both
        (D) TOPOLOGY: linear (ii) MOLECULE TYPE: cDNA (iii) HYPOTHETICAL: no (iii) ANTI-SENSE: no (vi) ORIGINAL SOURCE:
        (A) ORGANISM: Homo sapiens (xi) SEQUENCE DESCRIPTION: SEQ ID NO: 7:

```
CTAACGGGTG TGGTGGTGTG CACCTGTAGT CCCAGCTACT CGGGAGGCTG AGGCAGGAGA      60
ATCGCTTGAA CCCAGGAGGT GGAGGCTGCA GTGAGCCAAG ATCACGCCAC TGCACTCCAG     120
CCTGGGTGAC AGAGCAAGAC TCCATCTCAA CAACAACAAC AAAAAGGAAT TAAGGAGGAA     180
GCCACCTGGC TTCCTAAGAT AGACTTTATG GTTAATGGGA TTTATTTTAG CTGGTTAAGT     240
CCAGGACCCC TACCAGGAAG AACTGAGGTC CATATTTGAG GTTGGTCTCA CCCTTTTGCA     300
TGTGGTCCTA CTAATAATAA TTTTGCTGTA AGAAGCCTC AATAAGGAGA TGGACTGTGT      360
GAAAAGAGAT GAGAAAGCAG GCCTGTTTGC AAGGCTGGCC CTTGGCTGGC ATCTGAAAGC     420
TTGGATTTCA GGAGGGTTCT CATTACTCCC TAAATGATAA GAGTGGCTCA CTGTGCCTAA     480
ACTGTTCGTA CAAACAATGT GGGTTATGCC CAACATCTGC TTTCCTTCTG GGAGTCAGAT     540
TTTCATATGT GTTAGGCAGA GGATGAGGTG AGCAGCTCCC AATGAGAACC CTGAACACTG     600
AGTCTGTAAT GAGCTTCCCT TGTATACAAC ATTGCACATG GGTTGTCACA ACTGATTGCT     660
GGAGGAATTG TGTCCTATGT GACTCTGCTG GGAGAGGACT GTGGGAGGCT TACACCTGGT     720
TTCCCTGGAC TTTGTCCATG CGCTTTTTTC CTTTGCTGAT TTTGCTTCCT AGCCTTTCGC     780
TGTAGTAAAA CATAGCCATG AGTATGACTA CAGGCTGAGT CTGTGAATCT CCTAGTACAT     840
CATCAGACTA GGAGGTGGTG GTGTTGGCAC CCCCCAGCAC AGGGCACAAG GGAGACTTGC     900
AGGGTGTTTG TCATGTTCCC TTTCTCAATC TGGGTGTGGT TTACAGATTT GTTCAGTTTG     960
TGAAAATTCA CTGAGCTCTA TGAACAATTA TAATATGTAC ATTTTTTTCT GTAAGTGTAT    1020
TAAATTTCAA TAAAAGAAT TCACACTATA GGGGTACAAA ATAACTTAAT TTTTCAAAGT    1080
CTTCCTTTTA TTCAGCCAAC ATTTTAGTAA GTACCCTTTT TTTTTTACCA AGCACTGCTC    1140
TGGGAGCTTG GGACATGGGG TAGAAAGGAC GGCATCATTG TCCTCATTGT CCTTCAGCTT    1200
AGCTGCAAGG CAGGTGAAGG ATGCTTATAG TATGGTTGAT TTTTGCTGGG CTCTATGAAG    1260
GATCAGAGGG TGCTAAGGAG GCACAGAGAA AGAGCTTTTA ACGTGGGTAT TTTACTGTTC    1320
CAGGGTTGCC ACTCAAGTAC CTACAGAACA AACGGGTGTA GCTGTAAACT GTGGCAAACT    1380
GAAAGCATGT AGGCACAGAG TAAGTAGCTA GAGCTGATTT TTTTCAGGAA AGGCCACAAA    1440
TCCCAACTTT TATGAGCTCC TCTTTTAAAT GCTGTAAATG TTTTACAATG GCGGGGCGCG    1500
GTGGCTCACG CCTGTAATCC CAGCATTTGG GAGGCCGAGG GGCAGATCAC TTGAGGTCAG    1560
GAGTTCAAGA CCAGCCTGGC CAACATGGTG AAACCTCTTC TCTACTAAAA TTACAAAAAT    1620
TAGCCGGGCA TGGTGGTGCA TGCTTGTAAT TCCAGCTGCT AGGGAGGCCG AGGCGGGAGG    1680
ATTGCTTGAA CCCGGGAAGC AGAGGTTGCA GTGAGCTGAG ATCGTGCCAC TGCACTCCAG    1740
CCTGGGCGAC AGAGCAAGAT TCCGTCACAC ACACAAAAAA AAGGCGTGGG GGGAGGCCAA    1800
```

-continued

```
ACAAAACCCC GCAAGACACA TTTGGCTATG ACCTGCCAGT TTGCTAGGCA TTCTTCCAAC    1860

CTTCCCTCCC TCTGACCAAG AAACTGAGTG TCCACTATTT TAGGCCCTGG GAAATTCAGT    1920

AGCGAGGAGG CCAGACAGCT TCGTTGCATC ATGGGGGGCT CTGGTACTGT GCTTCTCCAA    1980

CTTCAGGATG TGTAGGAATC ACCTGAGCAG TCTTGTTGAG AGGCGGACAC TGACTCGGGA    2040

GGTCTGGGGT AGGGCCTGAA CGTTTGCCTT TGCGGTTCTA ACAAGCTCTC AGGTGATGGC    2100

GATGCTACTG TTCCCTGGCC CCGAGGTAGA GGAAGATTTA AGTAAAAGCT TCCTGGAGGA    2160

GGCGCAAGTG AACCGCAGGA GCTTTCCCGG ACGCCCGAGA AGGGAGAAAC CCCGAAGGAA    2220

TTCCTCCTCT CTCGGGGCTG GGTCTCCGCA TCCACGCCGG GTTTGGTTTC CCAGGCTATC    2280

CCACGTGTTC GGGCGTCCGT GTCAATCAGG TTTTCCCCGG CTGGGTCCGG GTTTAAAGGC    2340

TGCTGCTGCG CAGGGCGCTC CCATGGTGCC GCGCGGCGGG CGGGTTTGGA TTTTAAATCC    2400

CCGCGGCCAA TCAGTGGCGC GCAGGCTTTT GTAACGTTCC CAGCGCCGCG TTTGAATTCG    2460

GGGAGGAGCG GAGCGGTGCG GAGGCTCTGC TCGGATCGAG GTC                     2503
```

What is claimed is:

1. An isolated polypeptide comprising the amino acid sequence shown in SEQ ID NO:2.

* * * * *

UNITED STATES PATENT AND TRADEMARK OFFICE
CERTIFICATE OF CORRECTION

PATENT NO. : 6,180,380 B1
DATED : January 30, 2001
INVENTOR(S) : Klaus Strebhardt et al.

It is certified that error appears in the above-identified patent and that said Letters Patent is hereby corrected as shown below:

<u>Title page,</u>
Item [73], Assignee, please delete the caption and insert the following:
-- Klaus Strebhardt, Frankfurt; Helga Rübsamen-Waigmann, Bad Soden, all of (DE) --

Signed and Sealed this

Eleventh Day of May, 2004

JON W. DUDAS
*Acting Director of the United States Patent and Trademark Office*